United States Patent
Destarac et al.

(10) Patent No.: US 9,487,598 B2
(45) Date of Patent: Nov. 8, 2016

(54) LIVE POLY(N-VINYL LACTAM) REACTIVE STABILIZERS FOR DISPERSED PHASE POLYMERIZATION

(71) Applicant: RHODIA OPERATIONS, Paris (FR)

(72) Inventors: Mathias Destarac, Toulouse (FR); James Wilson, Coye la Foret (FR)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 14/375,328

(22) PCT Filed: Jan. 30, 2013

(86) PCT No.: PCT/EP2013/051788
§ 371 (c)(1),
(2) Date: Jul. 29, 2014

(87) PCT Pub. No.: WO2013/113750
PCT Pub. Date: Aug. 8, 2013

(65) Prior Publication Data
US 2015/0011657 A1    Jan. 8, 2015

(30) Foreign Application Priority Data

Jan. 31, 2012 (FR) .................................... 12 00291
Oct. 18, 2012 (FR) .................................... 12 02795

(51) Int. Cl.
| | | |
|---|---|---|
| C08F 226/10 | (2006.01) | |
| C08F 2/22 | (2006.01) | |
| C08F 26/06 | (2006.01) | |
| C08F 293/00 | (2006.01) | |
| C08F 2/20 | (2006.01) | |
| C08F 214/06 | (2006.01) | |
| C08F 214/18 | (2006.01) | |
| C08F 2/38 | (2006.01) | |
| C08F 218/08 | (2006.01) | |
| A61K 8/06 | (2006.01) | |
| A61K 8/81 | (2006.01) | |
| C09D 127/08 | (2006.01) | |
| C09D 131/04 | (2006.01) | |
| C09J 127/08 | (2006.01) | |
| C09J 131/04 | (2006.01) | |
| C09K 8/588 | (2006.01) | |

(52) U.S. Cl.
CPC . *C08F 2/22* (2013.01); *A61K 8/06* (2013.01); *A61K 8/8123* (2013.01); *A61K 8/8135* (2013.01); *C08F 2/20* (2013.01); *C08F 2/38* (2013.01); *C08F 26/06* (2013.01); *C08F 214/06* (2013.01); *C08F 214/18* (2013.01); *C08F 218/08* (2013.01); *C08F 293/005* (2013.01); *C09D 127/08* (2013.01); *C09D 131/04* (2013.01); *C09J 127/08* (2013.01); *C09J 131/04* (2013.01); *C09K 8/588* (2013.01); *A61K 2800/10* (2013.01); *C08F 226/10* (2013.01); *C08F 2438/03* (2013.01)

(58) Field of Classification Search
CPC ............. C08F 2/22; C08F 26/06; C08F 2/20
See application file for complete search history.

(56) References Cited

U.S. PATENT DOCUMENTS

| | | | |
|---|---|---|---|
| 6,153,705 A | 11/2000 | Corpart et al. | |
| 6,545,098 B1 | 4/2003 | Bouhadir et al. | |
| 6,777,513 B1 | 8/2004 | Destarac et al. | |
| 6,812,291 B1 | 11/2004 | Corpart et al. | |
| 2003/0045661 A1 | 3/2003 | Destarac et al. | |
| 2012/0004381 A1* | 1/2012 | Rizzardo et al. | ............. 526/204 |
| 2013/0289214 A1 | 10/2013 | Destarac et al. | |

FOREIGN PATENT DOCUMENTS

| | | |
|---|---|---|
| EP | 1510533 A1 | 3/2005 |
| EP | 1514884 A1 | 3/2005 |
| FR | 2794464 A1 | 12/2000 |
| FR | 2965264 A1 | 3/2012 |
| WO | WO 96/30421 A1 | 10/1996 |
| WO | WO 98/01478 A1 | 1/1998 |
| WO | WO 98/58974 A1 | 12/1998 |
| WO | WO 99/31144 A1 | 6/1999 |
| WO | WO 99/35177 A | 7/1999 |
| WO | WO 99/35178 A1 | 7/1999 |
| WO | WO 00/75207 A1 | 12/2000 |
| WO | WO 01/42312 A1 | 6/2001 |
| WO | WO 02/26836 A2 | 4/2002 |
| WO | WO 2010083569 A1 | 7/2010 |
| WO | WO 2013/113752 A1 | 8/2013 |

OTHER PUBLICATIONS

Dire, Charlotte, et al—"Nitroxide-Mediated Controlled/Living Free-Radical Surfactant-Free Emulsion Polymerization of Methyl Methacrylate Using a Poly(methacrylic acid)-Based Macroalkoxyamine Initiator", 2009, Macromolecules, vol. 42, pp. 95-103, American Chemical Society; 9 pgs.
Li, Wenwen, et al —"PEO-Based Block Copolymers and Homopolymers as Reactive Surfactants for AGET ATRP of Butyl Acrylate in Miniemulsion", 2008, Macromolecules, vol. 41, pp. 6387-6392, American Chemical Society; 6 pgs.
Ferguson, Christopher J., et al —"Effective ab Initio Emulsion Polymerization under RAFT Control", 2002, Macromolecules, vol. 35, Issue No. 25, Dec. 3, 2002, pp. 9243-9245, American Chemical Society; 3 pgs.
Rieger, Jutta, et al—"Surfactant-Free Controlled/Living Radical Emulsion (Co)polymerization of n-Butyl Acrylate and Methyl Methacrylate via RAFT Using Amphiphilic Poly(ethylene oxide)-Based Trithiocarbonate Chain Transfer Agents", 2009, Macromolecules, vol. 42, pp. 5518-5525, American Chemical Society; 8 pgs.

(Continued)

*Primary Examiner* — Robert Harlan
(74) *Attorney, Agent, or Firm* — Osha Liang LLP (57) ABSTRACT

The present invention concerns a method for preparing a polymer comprising a step (EI) for dispersed phase polymerization in the presence of a reactive stabiliser, wherein the following are brought into contact in an aqueous phase:—at least one ethylenically unsaturated monomer; —at least one source of free radicals; and—a reactive stabiliser comprising a polymer chain including monomer units (N-vinyl lactam) and a thiocarbonylthio-S group (C=S)—.

12 Claims, 1 Drawing Sheet

(56) References Cited

OTHER PUBLICATIONS

Taton, Daniel, et al—"Direct Synthesis of Double Hydrophilic Statistical Di-and Triblock Copolymers Comprised of Acrylamide and Acrylic Acid Units via the MADIX Process", 2001, Macromolecules Rapid Commun., vol. 22, Issue No. 18, pp. 1497-1503, Wiley-VCH Verlag GmbH; 7 pgs.

Yusa, Shi N-Ichi, et al—"Thermo-Responsive Diblock Copolymers of Poly(N-isopropylacrylamide and Poly(N-vinyl-2-pyrroridone) Synthesized via Organotellurium-Mediated Controlled Radical Polymerization (TERP)", 2007, vol. 40, pp. 5907-5915, American Chemical Society; 9 pgs.

U.S. Appl. No. 14/375,323, filed Jul. 29, 2014.

* cited by examiner

LIVE POLY(N-VINYL LACTAM) REACTIVE STABILIZERS FOR DISPERSED PHASE POLYMERIZATION

CROSS-REFERENCE TO RELATED APPLICATIONS

The present application is a U.S. national stage entry under 35 U.S.C. §371 of International Application No. PCT/EP2013/051788 filed Jan. 30, 2013, which claims priority to French Application No. 1200291 filed on Jan. 31, 2012 and French Application No. 1202795 filed on Oct. 18, 2012, the whole content of each of these applications being herein incorporated by reference for all purposes.

TECHNICAL FIELD OF THE INVENTION

The present invention relates to the field of polymerizations using monomers in a liquid phase dispersed in a continuous liquid phase (dispersed-phase polymerization), especially including emulsion polymerizations. More precisely, the invention relates to polymerizations of this type using particular stabilizers for the dispersed phase, known as "reactive stabilizers".

BACKGROUND OF THE INVENTION

Various polymerization reactions are known using monomers in the form of droplets dispersed in a continuous phase (generally an aqueous phase) with stabilizers of reactive stabilizer type.

In general, the reactive stabilizer used in these reactions is a molecule which can, firstly, stabilize the droplets of the dispersed phase containing the monomers, and which is also able to be engaged in the polymerization reaction. Such reactive stabilizers have, inter alia, the advantage of totally or partly replacing the additional surfactants that it is otherwise necessary to use in order to stabilize the dispersed phase, and they accordingly lead to polymer dispersions (latices) that are advantageous in the sense that they are free of such surfactants or at the very least in that they have a reduced content of such surfactants.

Such reactive stabilizers have especially been proposed for performing emulsion polymerizations of hydrophobic monomers of vinyl type, which are molecules of hydrophilic or amphiphilic nature typically comprising a hydrophilic polymer chain and a reactive group that is capable of inducing a controlled radical polymerization reaction of the monomers, for example of ATRP (atom transfer radical polymerization) or NMP (nitroxide-mediated polymerization), or RAFT or MADIX type in the presence of free radicals, with, for example, a group of xanthate type (bearing —S(C=S)O— functions) at the end of the chain. These reactive stabilizers ensure, firstly, the stabilization of the emulsion of droplets of the dispersed phase due to their hydrophilic nature, and they act, secondly, as polymerization control agent, typically via reversible addition-fragmentation transfer processes, via which the polymer chains grow from this control agent by gradual consumption of the monomers contained in each droplets, according to a process that is well known per se, in which the polymer chains have a "living" nature, in the sense that each step of incorporation of a monomer unit into the chain leads to a polymer which still bears a reactivable chain end for the subsequent incorporation of another monomer unit according to the same addition-fragmentation process (for further details regarding controlled or "living" radical polymerization and the production of chains growing from the transfer agent, reference may be made especially to the Handbook of RAFT polymerisation, Ed Barner-Kowollik C. Wiley-VCH 2008 or alternatively to the processes described in WO 96/30421, WO 98/01478, WO 99/35178, WO 98/58974, WO 00/75207 and WO 01/42312, WO 99/35177, WO 99/31144, FR2 794 464 or WO 02/26836).

Figure 1:
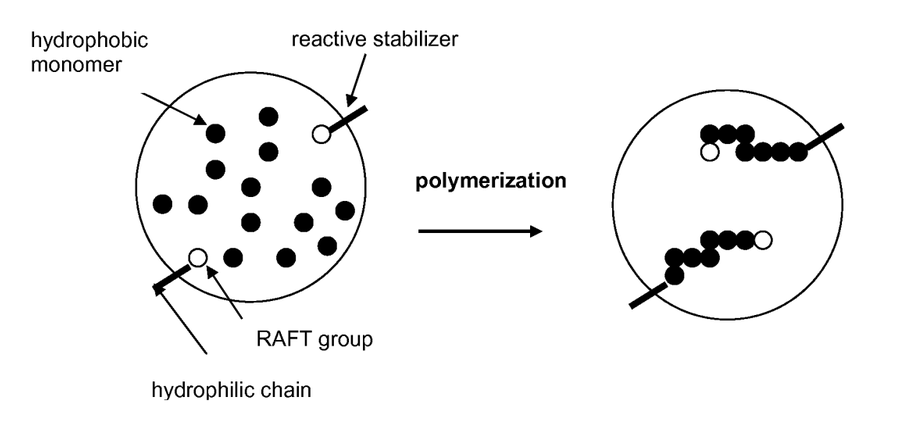
FIG. 1 illustrates the formation of living polymer chain in the dispersed droplets in accordance with one embodiment of the present invention.

With the reactive stabilizers of the abovementioned type, which induce a controlled radical polymerization, the formation of living polymer chains in the dispersed droplets is obtained, with an incorporation of the stabilizer into these polymer chains, from the very start of the polymerization, but while nevertheless conserving stabilization of the emulsion throughout the polymerization without necessarily having to use an additional surfactant, the hydrophilic chain schematically remaining permanently at the periphery of the droplets as illustrated in the attached FIG. 1.

Reactive stabilizers of the abovementioned type have especially been proposed in the processes described in the following publications:

Nitroxide-Mediated Controlled/Living Free-Radical Surfactant-Free Emulsion Polymerization of Methyl Methacrylate using a Poly(Methacrylic Acid)-based Macroalkoxyamine Initiator.
C. Dire, S. Magnet, L. Couvreur, B. Charleux
Macromolecules 42(1), 95-103 (2009)

PEO-based Block Copolymers and Homopolymers as Reactive Surfactants for AGET ATRP of Butyl Acrylate in Miniemulsion.
W. Li, K. Min, K. Matyjaszewski, F. Stoffelbach, B. Charleux
Macromolecules 41, 6387-6392 (2008)

Effective ab Initio Emulsion Polymerization under RAFT Control
Christopher J. Ferguson, Robert J. Hughes, Binh T. T. Pham, Brian S. Hawkett, Robert G. Gilbert, Algirdas K. Serelis, and Christopher H. Such
Macromolecules (2002)

Surfactant-free controlled/living radical emulsion (co)polymerization of n-butyl acrylate and methyl methacrylate via RAFT using amphiphilic poly(ethylene oxide)-based trithiocarbonate chain transfer agents.
J. Rieger, G. Osterwinter, C. Bui, F. Stoffelbach, B. Charleux
Macromolecules (2009)

Although advantageous in absolute terms, one of the limitations of the reactive stabilizers described hitherto is that they are suited only to the polymerization of certain vinyl monomers, essentially of methacrylate and alkyl acrylate type.

One aim of the present invention is to provide a dispersed-phase polymerization process suited to the use of a large number of hydrophobic monomers and especially suited to the dispersed-phase polymerization of vinyl esters and of hydrophobic N-vinyl monomers.

SUMMARY OF THE INVENTION

To this end, the present invention proposes the use of a novel type of reactive stabilizer, namely a living polymer chain derived from a RAFT or MADIX controlled radical polymerization of N-(vinyllactam) monomers.

More precisely, the subject of the present invention is a process for preparing a polymer, comprising a step (E1) of dispersed-phase polymerization in the presence of a reactive stabilizer, in which the following are placed in contact in an aqueous phase:

- at least one ethylenically unsaturated monomer, generally in dispersed form;
- at least one source of free radicals; and
- a reactive stabilizer comprising a polymer chain including (or even consisting of) N-(vinyllactam) monomer units and a thiocarbonylthio group —S(C=S)—, said step (E1) preferably being performed at a temperature below the degradation temperature of the thiocarbonylthio group —S(C=S)— of the reactive stabilizer, preferably at a temperature below 40° C., for example at a temperature of less than or equal to 30° C. (the process of the invention being able, for example, to be advantageously performed at room temperature).

The source of free radicals used in step (E1) is preferably a polymerization initiator of redox type. More generally, it may be any initiator that is capable of generating free radicals under the conditions of step (E1), preferably at a temperature below 40° C., more advantageously at a temperature of less than or equal to 30° C.

The dispersed-phase polymerization performed in the context of the invention is generally a polymerization which leads, at the end of the reaction, to an emulsion or a dispersion of the synthesized polymer in the aqueous phase.

To do this, according to a first embodiment, the monomers may typically be used in dispersed form in the aqueous phase (emulsion polymerization, for example).

Alternatively, the monomers may be used without any dispersion of monomer in the aqueous phase being formed. In this case, the polymer precipitates gradually and becomes dispersed in the form of particles (dispersion polymerization, typically). For example, the monomers may be introduced gradually in the course of the polymerization, while permanently maintaining a concentration of said monomers below their solubility limit.

According to a particular embodiment, the monomers may be introduced continuously or semicontinuously into an aqueous phase initially containing only a part of the monomers at an initial concentration below the solubility limit.

In any case, the reactive stabilizer used according to the invention can stabilize the polymer emulsion or dispersion obtained at the end of the reaction. In certain embodiments (especially emulsion polymerization), it can also stabilize the initial monomer dispersion.

The reactive stabilizer used in step (E1) is typically a polymer derived from a step (E0) of controlled radical polymerization of a composition comprising:

- monomers containing (and usually consisting of) identical or different (generally identical) N-vinyllactam monomers;
- a radical polymerization control agent, for example comprising a thiocarbonylthio group —S(C=S)—; and
- a radical polymerization initiator which is typically a redox system.

According to a particular embodiment of the invention, the radical polymerization initiator used may be a thermal system.

The studies that have been performed by the inventors on this subject have now made it possible to demonstrate that it turns out to be possible to perform a radical polymerization of N-vinyllactam monomer units both in aqueous medium and in an efficiently controlled manner, provided that this radical reaction is initiated by means of a redox system.

According to another embodiment, the reactive stabilizer used in step (E1) is prepared in organic solvent medium or without solvent. Where appropriate, it is replaced in water prior to step (E1).

The conditions of step (E1) of the invention are suited to the polymerization of a large number of ethylenically unsaturated monomers, including, inter alia, vinyl esters and other hydrophobic N-vinyl monomers. The invention gives access to other polymerizations, and it makes it possible especially to envisage the polymerization of the halogenated monomers described in greater detail hereinbelow in the present description.

After step (E1), stable polymer dispersions (latices) are generally obtained, with polymer particles of controlled mass and size, which constitutes another particular subject of the present invention. The invention may in particular give access to latices of fluorinated polyolefins (especially fluorovinyl polymers) free of fluorinated surfactants or at the very least having a surfactant content that is much lower than those commonly used.

Alternatively, if a small amount of monomers is used in step (E1), this step may lead to the formation of living polymers comprising a first block based on N-vinyllactam monomers onto which is grafted a small block based on hydrophobic units terminated with a thiocarbonylthio group —S(C=S)— (these living polymers being denoted hereinbelow by the term "grafted reactive stabilizers"). In this case, an aqueous medium is generally formed after step (E1), comprising these grafted reactive stabilizers regrouped into structures of micelle type which may especially be used as polymerization site for subsequent controlled radical polymerizations of generally hydrophobic ethylenically unsaturated monomers.

BRIEF DESCRIPTION OF THE DRAWING

For a detailed description of various embodiment of the invention, reference will now be made to the accompanying drawing, in which.

DETAILED DESCRIPTION OF THE INVENTION

Various advantageous features and embodiments of the process of the invention will now be described in greater detail.

The Reactive Stabilizer

The reactive stabilizers used in step (E1) may be used alone or in combination with other stabilizers. Thus, according to an advantageous embodiment, step (E1) is performed in the absence of other stabilizers, especially in the absence of surfactants. Nevertheless, according to another envisageable embodiment, step (E1) may be performed using the reactive stabilizers of the invention with other costabilizers, for example surfactants.

The reactive stabilizer used in step (E1) may typically be used at a mass concentration ranging from 0.01% to 50%.

The polymer/stabilizer mass ratio generally remains greater than 0.005, preferably greater than 0.01, for example greater than 0.02, especially to ensure a sufficient stabilizing effect. This polymer/stabilizer mass ratio generally does not need to be greater than 400, and it is typically less than or equal to 100, or even less than or equal to 50. Thus, this ratio may especially be between 0.005 and 400, for example between 0.05 and 300, especially between 0.02 and 50.

The N-vinyllactam Monomer Units of the Reactive Stabilizer

The monomers constituting the reactive stabilizer used in step (E1), and used, where appropriate, in step (E0), are ethylenically unsaturated monomers generally corresponding to the following formula:

in which n is an integer ranging from 2 to 6, typically equal to 3 (N-vinylpyrrolidone), 4 (N-vinylpiperidone) or 5 (N-vinylcaprolactam).

Preferably, the monomer units included in the reactive stabilizer used in step (E1) comprise N-vinylpyrrolidone (NVP). According to a particular embodiment, all of the monomers used in step (E) are NVP monomers. Other N-vinyllactam monomers may also prove to be advantageous according to the invention, among which mention may especially be made of, in a nonlimiting manner, N-vinylcaprolactam (NVCL).

The monomer units present in the reactive stabilizer used in step (E1) may, for example, consist exclusively of NVP monomer units, of NVCL monomer units or of a mixture of NVP or NVCL units (distributed in the form of blocks, in random form or in gradient form).

Alternatively, according to a possible embodiment, the N-vinyllactam monomers may comprise monomer units other than N-vinyllactams, which are typically introduced in step (E0) by copolymerizing the N-vinyllactam monomers with non-N-vinyllactam ethylenically unsaturated monomers, which typically leads to the formation of a random or gradient polymer block in step (E0). When monomer units other than N-vinyllactams are present in (E0), the content of N-vinyllactam monomers generally remains greater than or equal to 50%, more preferentially greater than or equal to 70% (for example at least 80%, or even at least 90%), by mass relative to the total mass of monomers used in step (E0).

Among the non-N-vinyllactam ethylenically unsaturated monomers that it may be advantageous to copolymerize with the N-vinyllactam monomers during step (E0), mention may be made especially of N-vinylimidazole (1-vinylimidazole), vinylcarbazole (N-vinylcarbazole), vinylphthalimide (N-vinylphthalimide), vinylacetamide (N-vinylacetamide), N-methyl-N-vinylacetamide, vinylformamide (N-vinylformamide) and vinyl esters. Other non-N-vinyllactam monomers may be used, among which mention may be made, in a nonlimiting manner, of acrylic acid, acrylamide, 2-acrylamido-2-methylpropanesulfonic acid (AMPS), acrylamidopropyltrimethylammonium chloride (APTAC), N,N-dimethylacrylamide, N-isopropylacrlamide (NIPAM), N,N-diethylacrylamide, diallyldimethylammonium chloride (DADMAC), vinylphosphonic acid, dialkylvinyl phosphonates, or vinyl sulfonate.

The Thiocarbonylthio Group of the Reactive Stabilizer

This group is typically introduced via the control agent used in the controlled radical polymerization performed in step (E0), which is typically a RAFT or MADIX control agent. According to a particular embodiment, this control agent used in step (E0) may bear several thiocarbonylthio groups.

The thiocarbonylthio group present on the reactive stabilizer typically corresponds to formula —S(C=S)—Z in which Z is as defined below, this group typically being obtained by using in step (E0) a control agent which corresponds to formula (A) below:

in which:
Z represents:
a hydrogen atom,
a chlorine atom,
an optionally substituted alkyl or optionally substituted aryl radical,
an optionally substituted heterocycle,
an optionally substituted alkylthio radical,
an optionally substituted arylthio radical,
an optionally substituted alkoxy radical,
an optionally substituted aryloxy radical,
an optionally substituted amino radical,
an optionally substituted hydrazine radical,
an optionally substituted alkoxycarbonyl radical,
an optionally substituted aryloxycarbonyl radical,
an optionally substituted carboxyl radical,
an optionally substituted aroyloxy radical,
an optionally substituted carbamoyl radical,
a cyano radical,
a dialkyl- or diaryl-phosphonato radical,
a dialkyl-phosphinato or diaryl-phosphinato radical,
or
a polymer chain,
and
$R_1$ represents:
an optionally substituted alkyl, acyl, aryl, aralkyl, alkene or alkyne group,
a saturated or unsaturated, aromatic, optionally substituted carbocycle or heterocycle, or
a polymer chain.

The groups $R_1$ or Z, when they are substituted, may be substituted with optionally substituted phenyl groups, optionally substituted aromatic groups, saturated or unsaturated carbocycles, saturated or unsaturated heterocycles, or groups chosen from the following: alkoxycarbonyl or aryloxycarbonyl (—COOR), carboxyl (—COOH), acyloxy (—O$_2$CR), carbamoyl (—CONR$_2$), cyano (—CN), alkylcarbonyl, alkylarylcarbonyl, arylcarbonyl, arylalkylcarbonyl, phthalimido, maleimido, succinimido, amidino, guanidimo, hydroxyl (—OH), amino (—NR$_2$), halogen, perfluoroalkyl $C_nF_{2n+1}$, allyl, epoxy, alkoxy (—OR), S-alkyl, S-aryl, groups of hydrophilic or ionic nature such as alkali metal salts of carboxylic acids, alkali metal salts of sulfonic acids, polyalkylene oxide chains (PEO, PPO), cationic substituents (quaternary ammonium salts), R representing an alkyl or aryl group, or a polymer chain.

According to a particular embodiment, $R_1$ is a substituted or unsubstituted, preferably substituted, alkyl group.

The optionally substituted alkyl, acyl, aryl, aralkyl or alkyne groups to which reference is made in the present description generally contain 1 to 20 carbon atoms, preferably 1 to 12 and more preferentially 1 to 9 carbon atoms. They may be linear or branched. They may also be substituted with oxygen atoms, especially in the form of esters or sulfur or nitrogen atoms.

Among the alkyl radicals, mention may be made especially of methyl, ethyl, propyl, butyl, pentyl, isopropyl, tert-butyl, pentyl, hexyl, octyl, decyl or dodecyl radicals.

For the purposes of the present description, the alkyne groups are radicals generally containing from 2 to 10 carbon atoms, and contain at least one acetylenic unsaturation, such as the acetylenyl radical.

For the purposes of the present description, the acyl groups are radicals generally containing from 1 to 20 carbon atoms with a carbonyl group.

Among the aryl radicals that may be used according to the invention, mention may be made especially of the phenyl radical, optionally substituted especially with a nitro or hydroxyl function.

Among the aralkyl radicals, mention may be made especially of the benzyl or phenethyl radical, optionally substituted especially with a nitro or hydroxyl function.

When $R_1$ or Z is a polymer chain, this polymer chain may be derived from a radical or ionic polymerization or derived from a polycondensation.

In the context of the present invention, it is especially advantageous to use, as control agents, xanthates, dithiocarbamates or dithiocarbazates.

Advantageously, use is made, as control agent in step (E0), of xanthate compounds, for instance O-ethyl-S-(1-methoxycarbonyl ethyl) xanthate of formula ($CH_3CH(CO_2CH_3)$)$S(C=S)OCH_2CH_3$, and, more generally, the reactive stabilizer of step (E1) preferably bears such groups.

A control agent that is particularly suited to the implementation of step (E0) is the compound sold by the company Rhodia under the name Rhodixan A1.

The Sources of Free Radicals that may be used in Steps (E0) and (E1)

The sources of free radicals used in steps (E0) and (E1) may be identical or different, and are typically identical for practical reasons.

A source of free radicals that is suitable both in step (E0) and in step (E1) is a polymerization initiator of redox type which comprises two agents, namely an oxidizing agent and a reducing agent, which may be introduced simultaneously or consecutively.

According to an advantageous embodiment, the reducing and oxidizing agents are introduced separately, which makes it possible to delay the initiation of polymerization until the second agent has been introduced. Advantageously, a step using such a redox agent is performed (i) by first forming a mixture comprising one of the oxidizing or reducing agents as a mixture with the monomers and the control agent (which is the reactive transfer agent in step (E1)) and then (ii) by adding to this mixture the other agent (reducing or oxidizing agent, respectively).

The advantageous effects revealed by the inventors in the context of the present invention are, in general, all the more pronounced the greater the difference between the standard redox potentials of the oxidizing agent and the reducing agent ($E_{ox}$-$E_{red}$). It is recommended in this context of the invention for the difference between the standard redox potentials of the oxidizing agent and of the reducing agent ($E_{ox}$-$E_{red}$) to be between 1 and 2 V. Moreover, in particular to avoid oxidation reactions of the N-vinyllactam monomers, it may be advantageous for the standard redox potential of oxidation $E_{ox}$ of the oxidizing agent (Ox) used in step (E0) to be less (preferably at least 0.2 V, more preferentially at least 0.5 V, or even at least 1 V) than that of the N-vinyllactam monomers used. More generally, it is preferable for the standard redox potential of oxidation $E_{ox}$ of the oxidizing agent (Ox) to be low enough so as not to oxidize the N-vinyllactam monomers. NVP monomers are most particularly sensitive to oxidation and it is preferable, when NVP is polymerized, for the oxidation potential $E_{ox}$ of the oxidizing agent to be less than 2 V, more preferentially less than 1.8 V, for example between 1.5 and 1.8 V.

Oxidizing agents that are particularly suited in this context are hydroperoxides, and especially tert-butyl hydroperoxide (t-BuOOH), which is especially advantageous when NVP monomers are polymerized. Hydrogen peroxide is another possible oxidizing agent.

Moreover, especially when the monomers used are monomers of NVP type, it is preferable for the agents present in the redox system not to contain acids that are of a nature to induce spurious reactions of the monomers, liable to lead to unwanted side products, and more generally for them not to contain compounds with a pKa low enough to induce such reactions. Thus, preferably, it is especially recommended to use reducing agents (Red) and oxidizing agents (Ox) which have a pKa of greater than 4, more preferentially greater than 6, or even 6.5, and preferably at least 7, which makes it possible to reduce the content of side products, generally at the very most to a few percent in the synthesized polymer. In this context, a reducing agent that is particularly suitable is sodium sulfite (pKa=7.2), which makes it possible, for example, to limit the content of side products to below 5% during the polymerization of NVP.

Redox systems that are particularly suited to performing steps (E0) and (E1) of the process of the invention comprise tert-butyl hydroperoxide (t-BuOOH) as oxidizing agent, combined with a reducing agent chosen from ascorbic acid and sodium sulfite.

The tert-butyl hydroperoxide/sodium sulfite redox system proves to be particularly advantageous, especially when the monomers used in step (E0) are or comprise NVP monomers. The use of this system in step (E0) makes it possible to polymerize NVP at room temperature and in water with a very low content of side products, typically remaining well below 5%.

The Conditions for Performing Steps (E0) and (E1)

Given the use of the redox system in step (E0), this step is advantageously performed in aqueous medium, typically using water as sole solvent. It thus makes it possible to obtain a polymer directly in aqueous medium without the need to use organic solvents, which makes the process particularly suited to use at the industrial scale.

Moreover, steps (E0) and (E1) are advantageously performed at low temperature, preferably below 40° C., more advantageously at a temperature of less than or equal to 30° C., especially between 5 and 25° C. These two steps may thus be performed, for example, at room temperature, which is another advantage of the process of the invention, in terms of energy costs.

The possibility of performing step (E0) at low temperature moreover makes it possible to envisage performing it for the polymerization of N-vinylcaprolactam (NVCL) in aqueous medium (in water or, advantageously, in a mixture of water and of a water-soluble solvent), which necessitates polymerization at a temperature below its cloud point, which is 32° C. In this context, the process of the invention may especially be performed for the synthesis of poly(N-vinylcaprolactam) or of polymers based both on amphiphilic or non-amphiphilic NVCL and NVP monomer units. These reactive stabilizers based on NVCL and NVP may also be synthesized in nonaqueous medium, and then used in water thereafter for (E1) after purification.

The block polymers prepared in steps (E0) and (E1) may be random (or gradient, in particular in step (E0)) homopolymers or copolymers.

The Monomers that may be used in (E1)

They are generally hydrophobic monomers.

Especially owing to the astute choice of a particular reactive stabilizer, the process of the invention proves to be modular and may be used for performing dispersed-phase polymerizations (especially emulsion polymerizations) of a very large number of ethylenically unsaturated hydrophobic monomers in step (E1).

Step (E1) in particular has the advantage of allowing the dispersed-phase polymerization of monomers of vinyl ester type. Thus, according to a first advantageous embodiment, the hydrophobic monomers that may be used in step (E1) may comprise vinyl ester monomers of formula $CH_2=CH-O-(C=O)-R_a$, in which $R_a$ represents:

an optionally substituted alkyl, acyl, aryl, aralkyl, alkene or alkyne group, preferably an alkyl group, a saturated or unsaturated, aromatic, optionally substituted carbocycle or heterocycle.

$R_a$ may especially be a linear or branched alkyl group, typically comprising from 1 to 20, for example from 4 to 18, carbon atoms, these alkyl groups possibly being optionally totally or partially halogenated (fluorinated and/or chlorinated).

Thus, step (E1) proves, for example, to be most particularly suited to the dispersed-phase polymerization of vinyl esters chosen from vinyl acetate, vinyl pivalate, vinyl butyrate, vinyl trifluoroacetate, vinyl stearate, or alternatively vinyl neodecanoate, and also mixtures of these monomers, with each other or with other ethylenically unsaturated monomers, optionally of vinyl ester type.

It should be noted on this subject that the reactive stabilizers of the invention prove to be suited to an emulsion polymerization of vinyl esters, for example in batch mode, especially given their transfer constant with respect to vinyl esters.

According to another embodiment, the hydrophobic monomers of step (E1) may comprise halogenated vinyl compounds, such as vinyl or vinylidene chlorides or fluoride, corresponding to the formula $R_bR_cC=CX^1X^2$, in which: $X^1=F$ or Cl $X^2=H$, F or Cl each one from among $R_b$ and $R_c$ represents, independently:

H, Cl, F; or an alkyl group, preferably chlorinated and/or fluorinated, more advantageously perchlorinated or perfluorinated.

The inventors have moreover demonstrated that the dispersed-phase polymerization of the abovementioned halogenated vinyl compounds may be obtained, more generally, with reactive stabilizers comprising a thiocarbonylthio group $-S(C=S)-$ similar to those of the present invention, but which contain a polymer chain other than a chain comprising monomer units (N-vinyllactam), or alternatively a chain comprising less than 50% or even less than 30% of monomer units (N-vinyllactam).

More precisely, the inventors have revealed an advantageous process for the dispersed-phase polymerization of halogenated vinyl compounds, corresponding to the formula $R_bR_cC=CX^1X^2$, in which: $X^1=F$ or Cl $X^2=H$, F or Cl each one from among $R_b$ and $R_c$ represents, independently:

H, Cl, F; or an alkyl group, preferably chlorinated and/or fluorinated, more advantageously perchlorinated or perfluorinated, in which these monomers are introduced into an aqueous phase, generally in dispersed form, together with at least one source of free radicals; and at least one reactive stabilizer referred to hereinbelow as "RS2" which comprises a polymer chain and a thiocarbonylthio group $-S(C=S)-$, this polymer chain comprising non-(N-vinyllactam) monomer units preferably chosen from:

hydrophilic monomers of acrylate type, for instance acrylic acid and salts thereof such as sodium acrylate, and also water-soluble acrylic acid esters, for instance 2-hydroxyethyl acrylate or oligo or polyethylene glycol acrylates;

hydrophilic monomers of acrylamido type, for instance acrylamide, dimethylacrylamide, 2-acrylamido-2-methyl-1-propanesulfonic acid and salts thereof, acrylamidopropyltrimethylammonium chloride (APTAC), dimethylaminopropylacrylamide, N,N-diethylacrylamide, N-isopropylacrylamide, N-morpholineacrylamide or N-hydroxyethylacrylamide;

hydrophilic monomers of methacrylate type, for example methacrylic acid and salts thereof such as sodium methacrylate and also oligo or polyethylene glycol methacrylates, 3-[N-(3-propyl methacrylate)-N,N-dimethyl]ammoniopropane sulfonate), hydroxyethyl methacrylate;

hydrophilic monomers of methacrylamido type, for instance methacrylamide, 3-[N-(3-methacrylamidopropyl)-N,N-dimethyl]ammoniopropane sulfonate (SPP), [(3-methacrylamidopropyl)-N,N-trimethylammonium chloride (MAPTAC);

hydrophilic monomers of vinyl type, for instance vinylphosphonic acid, sodium vinylsulfonate, 2-vinylpyridine, 4-vinylpyridine, and quaternized versions thereof, and vinylimidazole;

hydrophilic monomers of allylic type, for example diallyldimethylammonium chloride (DADMAC), diallyl dimethylammoniummethyl phosphonate (DALP);

optionally less than 50%, or even less than 30%, of N-vinyllactam monomer units.

With the abovementioned halogenated monomers, one of the advantages of the process of the invention proves to be particularly advantageous, namely the possibility of replacing the surfactants required in dispersed-phase polymerization with the reagents of the invention. Specifically, conventionally, the dispersed-phase polymerization of halogenated monomers of the abovementioned type involves the use of halogenated surfactants, which are usually fluorinated, such as fluoroamphiphiles of the type such as ammonium salts of perfluorooctanesulfonic acid (PFOS), of perfluorooctanoic acid (PFOA) or of perfluorononanoic acid (PFNA), the use of which is increasingly contested, due to their toxicological profile (toxicity associated with persistence).

These halogenated monomers may typically be used in step (E1) as described in the present invention, by replacing the N-vinyllactam reactive stabilizer with a reactive stabilizer of "RS2" type as defined above.

The invention makes it possible to provide fluorinated latices in which the surfactants of this type are at least partly and preferably totally replaced with reactive stabilizers according to the invention. In this context, the reactive stabilizers used may be halogenated or fluorinated (for example, use may be made of reactive stabilizers bearing fluorinated or chlorinated groups), but, unlike the usual dispersed-phase polymerization processes, the process of the invention, which uses reactive stabilizers, leads to immobilization of the stabilizers on the polymer particles, and therefore does not lead to the surfactant leaching effects that may be observed with the usual fluorinated latices. The invention thus permits in this context the use of fluorinated stabilizers with reduced impacts in terms of toxicity.

Moreover, the process of the invention affords access to a controlled polymerization of the abovementioned monomers that is particularly efficient and unprecedented in the case of the abovementioned halogenated monomers.

The halogenated monomers that may be used in step (E1) according to this second embodiment include, for example, vinyl chloride $H_2C=CHCl$ (VC), vinylidene chloride $H_2C=CCl_2$ (VC2), vinyl fluoride (VF), vinylidene fluoride (VDF), hexafluoropropene (HFP), 3,3,3-trifluoropropene (TFP), tetrafluoroethylene (TFE), chlorotrifluoroethylene (CTFE), or perfluorovinyl ethers (PFVE), for instance perfluoromethyl vinyl ether (PFMVE). These monomers may be homopolymerized or copolymerized in step (E1), with each other, or with other ethylenically unsaturated, halogenated or non-halogenated monomers (typically less than 50 mol % of non-halogenated monomer, where appropriate).

The Polymer Dispersions Synthesized According to the Invention

Irrespective of the nature of the monomers used, step (E1) affords access to polymer dispersions. Typically, it is a latex comprising dispersed particles formed from block polymers derived from the controlled radical polymerization, as obtained after step (E1), which contain dispersed particles formed from block polymers derived from the controlled radical polymerization performed in this step, each of these block polymers comprising:

a first block, which is generally hydrophilic, or optionally amphiphilic, corresponding to the polymer chain based on poly(N-vinyllactam) units of the reactive stabilizers used in step (E1); and
  covalently bonded to this first block, a second block, which is hydrophobic, comprising a polymer chain resulting from the polymerization of the ethylenically unsaturated monomers used in step (E1), generally terminating with the thiocarbonylthio reactive group (for example xanthate) initially present on the reactive stabilizer used in step (E1).

Taking into account the operating conditions of step (E1), the block polymers derived from this step become arranged, schematically, in each particle to form a particle "core" based on hydrophobic blocks and an outer "shell" based on the poly(N-vinyllactam) polymer chains, covalently bonded to the chains of the core.

The latices thus obtained have the advantage of being stable without requiring the presence of surfactants. Although the use of an additional surfactant is not excluded, it is usually advantageous that no additional surfactant be used in step (E1) or subsequently thereto, which makes it possible to obtain surfactant-free latices. The immobilization of the stabilizer on the particle by covalent grafting, intrinsic to the use of step (E1), participates toward the stabilization of the latex, by inhibiting the desorption phenomena that are observed when the usual surfactants are used instead of the reactive stabilizers of the invention.

Moreover, the use of step (E1) makes it possible to obtain controlled surface chemistry at the surface of the latex particles, which is modulable depending on the nature of the polymer chain of the reactive stabilizers onto which reactive groups may be introduced:

before step (E1): especially by introducing functionalized or non-functionalized monomers, in step (E0), for example by copolymerizing in step (E0) the N-vinyllactams with other monomers, chosen, for instance, from acrylamides, N,N-dimethylacrylamides, 2-acrylamido-2-methylpropanesulfonic acid (AMPS), acrylamidopropyltrimethylammonium chloride (APTAC) or acrylic acid; and/or
  after step (E1): for example by grafting reaction via groups present on the poly(N-vinyllactam) polymer chains immobilized at the surface of the latex particles.

The use of controlled radical polymerization in step (E1) moreover allows extremely fine control of the number-average molecular mass Mn of the synthesized polymers, in a very simple and direct manner. As a result, step (E1) allows very easy fine control of the size of the particles formed, which may be used especially for optimizing the colloidal stability. Furthermore, polymer particles are obtained which tend, in the same manner, to have homogeneous and narrow diameters about a mean value.

The polymers obtained according to step (E1) in the form of particles have a living nature and may thus, in absolute terms, be used as living polymers for the subsequent synthesis of block copolymers onto which a third block will be grafted. In this context, the polymers obtained in step (E1) may be used as control agents in a polymerization step subsequent to step (E1).

Usually, however, these polymers are used in latex form. In this case, it may be desirable to deactivate the reactive end of the polymers obtained after step (E1). This deactivation may be performed after step (E1), or alternatively it may terminate this step (for example, it may be performed when the desired molecular mass or the expected diameter of the latex particles is reached). In this context, the process then comprises, after step (E1), a step (E2) of chemical treatment of the end of the chain. For example, when the reactive stabilizer used in step (E1) is a xanthate, the xanthate reactive end obtained on the polymer may be deactivated to deprive the polymer of its living nature, for example via the action of hydrogen peroxide or via the action of an organoperoxide or alternatively of ozone, which oxidizes the xanthate reactive end into various oxidized species (especially of thioester type —S(C=O)— and —SO$_3$H).

According to a specific embodiment, the polymer chain of the reactive stabilizer used in step (E1) is based on monomers which are capable of ensuring the colloidal stability of the latex particles under certain conditions, but which lose this property (or undergo a reduction in this property) under other conditions (for example under the effect of a change of temperature, pH or salinity), whereby the latex obtained is sensitive to a stimulus in which flocculation of the latex is obtained. By way of example, an effect of this type is obtained for reactive stabilizers of poly(N-vinylcaprolactam) type for which colloidal stability is obtained at low temperature and flocculation is obtained above a threshold temperature.

The latices obtained after step (E1) may be used in a very large number of applications, especially for producing paints, coatings and adhesives, for preparing construction materials, or alternatively in cosmetic or body care compositions, in plant protection formulations or for the agricultural sector, or alternatively in petroleum extraction fluids.

According to a particular embodiment, the polymer dispersion obtained from step (E1) which comprises block polymers derived from the controlled radical polymerization as obtained after step (E1), organized in the form of micelles, which may be used as a site of polymerization for controlled radical polymerizations.

The invention and the advantages thereof will be further illustrated by the implementation examples given below.

EXAMPLES

Example 1

Preparation of an NVP-Xa Reactive Stabilizer 120 g of N-vinylpyrrolidone, 60 g of distilled water, 9 g of O-ethyl-S-(1-methoxycarbonylethyl) xanthate of formula $(CH_3CH(CO_2CH_3))S(C=S)OEt$ and 2.1 g of a tert-butyl hydroperoxide solution (70% by mass in water) were placed in a 250 ml round-bottomed flask at room temperature (20° C.).

The reaction mixture was degassed by sparging with pure nitrogen for 30 minutes. Next, 2.1 g of sodium sulfite were added in a single portion under a stream of nitrogen.

The reaction medium was then left stirring for 24 hours at room temperature.

After the reaction, a conversion of 95% was determined by $^1$H NMR. The presence of the xanthate end is also observed by $^1$H NMR.

Example 2

Dexanthatation of the Reactive Stabilizer NVP-Xa→NVP 30 g of the solution of NVP-Xa were placed in a 100 ml round-bottomed flask at room temperature (20° C.). The mixture was heated at 90° C. for 5 hours with stirring. The removal of the xanthate chain end was confirmed by a UV/VIS spectrophotometric analysis. The disappearance of the peak at 262 nm, which is characteristic of $CS(C=S)OEt$, demonstrates a successful dexanthatation.

Example 3

Emulsion Polymerization of Vinyl Acetate in the Presence of NVP-Xa 10 g of vinyl acetate, 90 g of distilled water, 0.42 g of NVP-Xa (Example 1) and 0.14 g of a tert-butyl hydroperoxide solution (70% by mass in water) were placed in a 250 ml round-bottomed flask at room temperature (20° C.).

The reaction mixture was degassed by gentle sparging with pure nitrogen for 5 minutes.

Next, 0.1 g of sodium sulfite was added in a single portion under a stream of nitrogen.

The reaction medium was then left stirring for 12 hours at room temperature.

After the reaction, a conversion of 89% was determined by gravimetry.

Analysis by static light scattering (Malvern Zetasizer) gives a particle diameter value Dz of 123 nm and a particle polydispersity value of 0.01.

Example 4

Emulsion Polymerization of Vinyl Acetate in the Presence of NVP-Xa 10 g of vinyl acetate, 90 g of distilled water, 4.2 g of NVP-Xa (Example 1) and 0.14 g of a tert-butyl hydroperoxide solution (70% by mass in water) were placed in a 250 ml round-bottomed flask at room temperature (20° C.).

The reaction mixture was degassed by gentle sparging with pure nitrogen for 5 minutes.

Next, 0.1 g of sodium sulfite was added in a single portion under a stream of nitrogen.

The reaction medium was then left stirring for 12 hours at room temperature.

After the reaction, a conversion of 81% was determined by gravimetry.

Analysis by static light scattering (Malvern Zetasizer) gives a particle diameter value Dz of 36 nm and a particle polydispersity value of 0.2.

Example 5

Emulsion Polymerization of Vinyl Acetate in the Presence of NVP-Xa 37.04 g of vinyl acetate, 90 g of distilled water, 1.56 g of NVP-Xa (Example 1) and 0.53 g of a tert-butyl hydroperoxide solution (70% by mass in water) were placed in a 250 ml round-bottomed flask at room temperature (20° C.).

The reaction mixture was degassed by gentle sparging with pure nitrogen for 5 minutes.

Next, 0.37 g of sodium sulfite was added in a single portion under a stream of nitrogen.

The reaction medium was then left stirring for 12 hours at room temperature. At the end of the reaction, a coagulum-free stable latex was obtained.

After the reaction, a conversion of 97% was determined by gravimetry.

Example 6

Emulsion Polymerization of Vinyl Acetate in the Presence of Xanthate-Freed NVP (Example 2)

37.04 g of vinyl acetate, 90 g of distilled water, 1.56 g of NVP (Example 2) and 0.53 g of a tert-butyl hydroperoxide solution (70% by mass in water) were placed in a 250 ml round-bottomed flask at room temperature (20° C.).

The reaction mixture was degassed by gentle sparging with pure nitrogen for 5 minutes.

Next, 0.37 g of sodium sulfite was added in a single portion under a stream of nitrogen.

The reaction medium was left stirring.

After 180 minutes, it was observed that the latex was totally flocculated.

Example 7

Emulsion Polymerization of Vinylidene Chloride (VDC) in the Presence of NVP-Xa 10 g of VDC, 59 g of distilled water, 0.43 g of NVP-Xa (Example 1) and 0.27 g of a tert-butyl hydroperoxide solution (70% by mass in water) were placed in a 250 ml round-bottomed flask at room temperature (20° C.).

The reaction mixture was cooled to 10° C. and degassed by gentle sparging with pure nitrogen for 5 minutes with stirring (magnetic bar). Next, 0.26 g of sodium sulfite was added in a single portion under a stream of nitrogen.

The reaction medium was then left stirring for 3 hours at 10° C. (±5° C.).

After the reaction, a conversion of 87% was determined by gravimetry.

Analysis by static light scattering (Malvern Zetasizer) gives a particle diameter value Dz of 222 nm and a particle polydispersity value of 0.03.

Example 8

Emulsion Polymerization of Vinylidene Chloride (VDC) in the Presence of NVP-Xa 10 g of VDC, 59 g of distilled water, 1.31 g of NVP-Xa (Example 1) and 0.27 g of a tert-butyl hydroperoxide solution (70% by mass in water) were placed in a 250 ml round-bottomed flask at room temperature (20° C.).

The reaction mixture was cooled to 10° C. and degassed by gentle sparging with pure nitrogen for 5 minutes with stirring (magnetic bar). Next, 0.26 g of sodium sulfite was added in a single portion under a stream of nitrogen.

The reaction medium was then left stirring for 3 hours at 10° C. (±5° C.).

After the reaction, a conversion of 87% was determined by gravimetry.

Analysis by static light scattering (Malvern Zetasizer) gives a particle diameter value Dz of 192 nm and a particle polydispersity value of 0.01.

Example 9

Emulsion Polymerization of Vinylidene Chloride (VDC) in the Presence of Polyacrylamide-Xa 10 g of VDC, 59 g of distilled water, 0.47 g of Polyacrylamide-Xa (Xa=Rhodixan A1, Mn=3000 g/mol, synthesized according to Taton et al. Macromol. Rapid Commun. 2001, 22, 18, 1497) and 0.26 g of a tert-butyl hydroperoxide solution (70% by mass in water) were placed in a 250 ml round-bottomed flask at room temperature (20° C.).

The reaction mixture was cooled to 10° C. and degassed by gentle sparging with pure nitrogen for 5 minutes with stirring (magnetic bar). Next, 0.26 g of sodium sulfite was added in a single portion under a stream of nitrogen.

The reaction medium was then left stirring for 3 hours at 10° C. (±5° C.).

After the reaction, a conversion of 91% was determined by gravimetry.

Analysis by static light scattering (Malvern Zetasizer) gives a particle diameter value Dz of 241 nm and a particle polydispersity value of 0.04.

Example 10

Emulsion Polymerization of Vinylidene Chloride (VDC) in the Presence of Poly(acrylic acid)-Xa 10 g of VDC, 59 g of distilled water, 0.47 g of Polyacrylic acid-Xa (Xa=Rhodixan A1, Mn=3200 g/mol, synthesized according to Taton et al. Macromol. Rapid Commun. 2001, 22, 18, 1497) and 0.26 g of a tert-butyl hydroperoxide solution (70% by mass in water) were placed in a 250 ml round-bottomed flask at room temperature (20° C.).

The reaction mixture was cooled to 10° C. and degassed by gentle sparging with pure nitrogen for 5 minutes with stirring (magnetic bar). Next, 0.26 g of sodium sulfite was added in a single portion under a stream of nitrogen.

The reaction medium was then left stirring for 3 hours at 10° C. (±5° C.).

After the reaction, a conversion of 89% was determined by gravimetry.

Analysis by static light scattering (Malvern Zetasizer) gives a particle diameter value Dz of 195 nm and a particle polydispersity value of 0.03.

The invention claimed is:

1. A process for preparing a polymer, comprising a step (E1) of dispersed-phase polymerization in the presence of a reactive stabilizer, wherein the following are placed in contact in an aqueous phase:
    at least one ethylenically unsaturated monomer;
    a redox initiator comprising tert-butyl hydroperoxide as oxidizing agent, combined with a reducing agent selected from the group consisting of ascorbic acid and sodium sulfite; and
    a reactive stabilizer comprising a polymer chain including N-(vinyllactam) monomer units and a thiocarbonylthio group —S(C=S)—;
    wherein step (E1) is performed in the absence of surfactants.

2. The process as claimed in claim 1, wherein in said step (E1), the ethylenically unsaturated monomer is in dispersed form.

3. The process as claimed in claim 1, wherein said step (E1) is performed at a temperature below 40° C.

4. The process as claimed claim 1, wherein in the reactive stabilizer used in said step (E1), N-(vinyllactam) monomer units generally correspond to the following formula:

wherein n is an integer ranging from 2 to 6.

5. The process as claimed in claim 4, wherein in the reactive stabilizer used in said step (E1), is monomers N-vinylpyrrolidone, N-vinylpiperidone or N-vinylcaprolactam.

6. The process as claimed in claim 1, wherein the thiocarbonylthio group present on the reactive stabilizer is a xanthate or a dithiocarbamate.

7. The process as claimed in claim 1, wherein the ethylenically unsaturated monomers used in said step (E1) are vinyl ester monomers of formula $CH_2=CH-O-(C=O)-R_a$, wherein $R_a$ represents:
    an optionally substituted alkyl, acyl, aryl, aralkyl, alkene or alkyne group,
    a saturated or unsaturated, aromatic, optionally substituted carbocycle or heterocycle.

8. The process as claimed in claim 1, wherein the ethylenically unsaturated monomers used in said step (E1) comprise halogenated vinyl compounds, corresponding to the formula $R_bR_cC=CX^1X^2$, wherein: $X^1$=F or Cl $X^2$=H, F or Cl each one from among $R_b$ and $R_c$ represents, independently:
H, Cl, F; or
an alkyl group.

9. A polymer dispersion obtained according to the process of claim 1.

10. The dispersion as claimed in claim 9 is a latex comprising dispersed particles formed from block polymers derived from the controlled radical polymerization as obtained after said step (E1) of claim 1.

11. A method for producing paints, coatings and adhesives, for preparing construction materials, in cosmetic or body care compositions, in plant protection formulations or for the agricultural sector, or in petroleum extraction fluids, said method comprising a step of using said dispersion as claimed in claim 10.

12. The dispersion as claimed in claim 9 comprises block polymers derived from the controlled radical polymerization as obtained after said step (E1) of claim 1, organized in the form of micelles, which may be used as a site of polymerization for controlled radical polymerizations.

* * * * *